United States Patent [19]

Murai et al.

[11] Patent Number: 4,918,005

[45] Date of Patent: Apr. 17, 1990

[54] METHOD OF QUANTITATIVE ASSAY FOR VITAMIN $B_{12}$ AND REAGENT FOR ASSAYING VITAMIN $B_{12}$

[75] Inventors: Asao Murai, Kawasaki; Masao Yamamoto, Tokyo, both of Japan

[73] Assignee: Sanraku Incorporated, Tokyo, Japan

[21] Appl. No.: 74,745

[22] Filed: Jul. 17, 1987

[30] Foreign Application Priority Data

Jul. 25, 1986 [JP] Japan .................... 61-175332

[51] Int. Cl.⁴ ............ C12Q 1/04; C12Q 1/00; C12R 1/89; G01N 33/567
[52] U.S. Cl. ............................ 435/34; 435/4; 435/29; 435/39; 436/505
[58] Field of Search ............ 435/4, 29, 30, 34, 39, 435/853, 946; 436/505

[56] References Cited

U.S. PATENT DOCUMENTS 4,188,189 2/1980 Allen .............................. 435/7

FOREIGN PATENT DOCUMENTS 0251767 11/1970 U.S.S.R. .......................... 436/505

OTHER PUBLICATIONS

Y. Masao, "Application of a Marine Methanol–Utilizing Bacterium for Bioassay of Vitamin $B_{12}$ in Sea Water"

Chemical Abstracts, vol. 92, No. 14, Apr. 17, 1980, p. 329, Abstract No. 116045x.

Primary Examiner—Robert J. Warden
Assistant Examiner—Laurie A. Scheiner
Attorney, Agent, or Firm—Jordan and Hamburg

[57] ABSTRACT

The present invention is directed to a method of quantitative assay for a vitamin $B_{12}$-containing substance which comprises culturing marine methanol-utilizing bacteria having $B_{12}$ auxotrophy in a medium for quantitative assay of the bacteria containing pyrroloquinoline-quinone and a polyoxyethylene sorbitan fatty acid ester and, quantitatively determining vitamin $B_{12}$ in the vitamin $B_{12}$-containing substance as a function of the degree of growth thereof and, to a reagent for the $B_{12}$-containing substance comprising a kit for combination of an ampule or vial having sealed therein a dry viable bacteria composition of a marine methanol-utilizing bacteria for inoculation and an ampule or vial having sealed therein a medium for the bacteria containing pyrroloquinoline-quinone and a polyoxyethylene sorbitan fatty acid ester, or in addition thereto, further an ampule or vial having sealed therein a standard dilution of vitamin $B_{12}$ having a serial concentration.

6 Claims, No Drawings

METHOD OF QUANTITATIVE ASSAY FOR VITAMIN $B_{12}$ AND REAGENT FOR ASSAYING VITAMIN $B_{12}$

BACKGROUND OF THE INVENTION

1. Field of the Invention

The present invention relates to a method of quantitative microorganism assay for a vitamin $B_{12}$ (hereafter simply referred to as $B_{12}$)-containing substance and a reagent used for the method of quantitative assay. More particularly, the present invention relates to a method of quantitative assay of $B_{12}$ in a $B_{12}$-containing substance using marine methanol-utilizing bacteria requiring $B_{12}$ for growth and capable of assimilating methanol quickly in a simple manner and a reagent for quantitative assay of the $B_{12}$-containing substance comprising a composition of dry viable bacteria for inoculation of marine methanol-utilizing bacteria having $B_{12}$ auxotrophy used for the quantitative assay and a liquid medium containing methanol and also containing pyrroloquinoline-quinone and a polyoxyethylene sorbitan fatty acid ester and a $B_{12}$ standard solution.

2. Brief Description of the Prior Art

Physicochemical methods and microbiological methods have been hitherto known as quantitative assay for $B_{12}$-containing substances, i.e., substances containing vitamin $B_{12}$. Among the microbiological methods, a method of quantitatively determining $B_{12}$ in $B_{12}$-containing substances using marine methanol-utilizing bacteria requiring $B_{12}$ for growth is known to be excellent (Published Unexamined Japanese Patent Application No. 19022/1980).

When an attempt is made to quantitatively determine $B_{12}$ in $B_{12}$-containing substances, however, this method is disadvantageous in that bacteria do not necessarily have stable growth and the $B_{12}$ cannot be quantitatively determined quickly with accuracy.

Problems to be solved by the present invention are in the development of an improved method for quantitatively assaying a $B_{12}$-containing substance that eliminates the defects possessed by conventional assay methods of $B_{12}$-containing substances using marine methanol-utilizing bacteria having $B_{12}$ auxotrophy, namely, failing to quantitatively determine the $B_{12}$-containing substance stably and quickly with good accuracy, and reagents for quantitative assay for $B_{12}$.

As a result of various investigations to solve the foregoing problems, the present inventors have found that by supplementing pyrroloquinoline-quinone and a polyoxyethylene sorbitan fatty acid ester to a medium for quantitative assay using marine methanol-utilizing bacteria having $B_{12}$ auxotrophy, the $B_{12}$ in a $B_{12}$-containing substance can be quantitatively determined stably with accuracy. The present invention has been accomplished based on this finding.

SUMMARY OF THE INVENTION

An object of the present invention is to provide a quick and simple method of quantitative assay for $B_{12}$-containing substances, i.e., substances containing vitamin $B_{12}$, using marine methanol-utilizing bacteria.

Another object of the present invention is to provide a reagent used in a quantitative assay for $B_{12}$-containing substances using marine methanol-utilizing bacteria.

The method of quantitative assay for a vitamin $B_{12}$-containing substance according to the present invention is characterized by culturing marine methanol-utilizing bacteria having $B_{12}$ auxotrophy in a medium for quantitative assay for the bacteria containing pyrroloquinoline-quinone and a polyoxyethylene sorbitan fatty acid ester, and quantitatively determining vitamin $B_{12}$ depending upon degree of growth thereof.

The present invention is also directed to a reagent for quantitative assay used in microbiological assay for a $B_{12}$-containing substance, comprising a kit for combination of an ampule or vial having sealed therein a dry viable bacteria composition of marine methanol-utilizing bacteria having $B_{12}$ auxotrophy for inoculation and an ampule or vial having sealed therein a medium for quantitative assay for the bacteria containing pyrroloquinoline-quinone and a polyoxyethylene sorbitan fatty acid ester, or further an ampule or vial having sealed therein a standard dilution of vitamin $B_{12}$ having a serial concentration.

DETAILED DESCRIPTION OF THE INVENTION

As microorganisms which can be used in accordance with the present invention, mention may be made of *Alteromonas thalassomethanolica* YK 4007, FERM BP-1401 (This strain deposited under FERM P-3621 on June 22, 1976 at Fermentation Research Institute, Agency of Industrial Science and Technology, 1-3, Higashi, 1-chome, Yatabe-machi, Tsukuba-gun, Ibaraki-ken, Japan and Transferred on July 2, 1987 to International deposition FERM BP-1401 under the treaty on the International Recognition of the Deposit of Microorganisms for the purpose of patent procedure. Its bacteriological properties are described in J. Ferment. Technol., 58, 99–106 (1980)) which has already been separated as a marine methanol-utilizing bacteria based on characteristics that the bacteria can be well assimilated using methanol as only one carbon source and seawater can be utilized as water for the medium, etc.; and the like. All of these microorganisms are characterized by requiring $B_{12}$ for growth.

As media for quantitatively assaying the $B_{12}$-containing substance that can be used in the present invention, conventional media for quantitatively assaying marine methanol-utilizing bacteria having $B_{12}$ auxotrophy heretofore used are usable except for that containing pyrroloquinoline-quinone and the polyoxyethylene sorbitan fatty acid ester. Additional incorporation of iron sulfates, zinc sulfates, sodium thiosulfate, thioglycolic acid, etc. in the media having the aforesaid composition for quantitative assay give good assay results on some occasions.

It is desired that the amount of pyrroloquinoline-quinone to be incorporated is in the range of 10 to 60 ng per 100 ml of the medium for quantitative assay; when the amount exceeds 75 ng, good assay results cannot always be obtained because the growth of the microorganism is inhibited. Further when the amount is less than 10 ng, good assay results cannot always be obtained because of uneven growth of the microorganism.

Preferably, the amount of the polyoxyethylene sorbitan fatty acid ester to be incorporated should be in the range of 1 to 20 mg based on 100 ml of the medium for quantitative assay; when the amount exceeds 20 mg, the growth of the microorgansim is sometimes inhibited and when the amount is less than 1 mg, uneven growth is noted and good results cannot always be obtained.

The inoculant that can be used in the present invention may be used by preincubating the bacteria used in the liquid medium, collecting the bacteria and washing, as in conventional microbiological methods; the inoculant may also be used without preincubation, by collecting the bacteria grown on agar in a conventional manner and washing. It is also a characteristic of the present invention that the quantitative assay can be performed in a simpler manner.

In the quantitative assay method of the present invention, no growth of bacteria is observed with a variety of substances that lack $B_{12}$ activity for example, yeast extract that contains DL-methionine which is an amino acid, thymidine which is one of nucleic acid components, $\beta$-aminolevulinic acid which is a precursor of biosynthesis, cobalt salts which are constituents of $B_{12}$, various amino acids, peptides, vitamins and nucleic acids, which do not contain $B_{12}$, etc.; growth of the bacteria is observed with meat extract containing $B_{12}$. From such it is clear that $B_{12}$ in a containing substance, 3.g., meat extract, can be specifically determined quantitatively according to the assay method of the present invention.

The microorganism used in the present invention can be dried while maintaining a live state and the composition of the dry bacteria can be stored over a long period of time while the microorganism is in a live state. Accordingly, when the viable bacteria are dried and stored, the dry composition can be readily suspended in a medium solution or sterilized water upon quantitative assay for the $B_{12}$-containing substance and the bacteria suspension can be used directly as an inoculated bacteria solution for quantitative assay. Further, the liquid culture solution for quantitative assay can be aseptically stored over a long period of time, sealed in, for example, an ampule, a glass bottle, etc., stored, unsealed depending upon necessity and provided for assay as a set or kit together with the composition of the dry bacteria for inoculation described above. For this reason, the composition of the bacteria and a predetermined amount of the medium for quantitative assay comprising pyrroloquinoline-quinone and the polyoxyethylene sorbitan fatty acid ester can be provided as an assay device; when assaying the $B_{12}$-containing substance quantitatively using the reagent, it can be accomplished in an extremely simple manner without requiring storage and control of the bacterial strain. Further, an automated bioassay device can be constructed by incorporating the bacteria composition and the medium for quantitative assay in accordance with the present invention into the device, respectively to quantitatively assay the $B_{12}$-containing substance automatically. To dry the viable bacteria, a solution of 10 g of sodium chloride, 20 g of sodium glutamate and 0.2 g of magnesium sulfate in 1 liter of M/30 phosphate buffer is used as a dispersion medium and the washed viable bacteria is suspended in the dispersion medium followed by freeze drying. It is advantageous that the medium for quantitative assay be stored and supplied as an ampule because such is free from evaporation and dissipation of methanol. The bacteria are resistant to salts, grow using methanol as only one carbon source and are insensitive to compounds other than $B_{12}$ so that even extremely rough operation can give accurate analytical data.

Next the present invention will be described by referring to the examples.

EXAMPLE 1

A medium for storing a bacterial strain was prepared as follows. To 1 liter of water were added 2 g of ammonium sulfate, 0.3 g of magnesium sulfate, 1 g of potassium primary phosphate, 5.5 g of potassium secondary phosphate, 30 g of sodium chloride, 0.5 g of meat extract and 15 g Of Agar. After sterilizing at 120° C. for 5 minutes, 5 ml of methanol was added before agar was solidified. The system was separately poured in sterilized test tubes, which were slanted and solidified to make a slant, respectively. An assay medium was prepared by sterilizing 1 liter of a medium for quantitative assay having a composition shown in Table 1 at 120° C. for 5 minutes, adding 2.5 ml of methanol thereto and separately pouring the medium for quantitative assay into an L-shaped tube by 9 ml each.

TABLE 1

| Component | Medium A (/l) | Medium B (/l) |
|---|---|---|
| Ammonium sulfate | 1 g | 1 g |
| Magnesium sulfate | 0.3 g | 0.3 g |
| Potassium primary phosphate | 2 g | 2 g |
| Potassium secondary phosphate | 7 g | 7 g |
| Sodium chloride | 30 g | 30 g |
| Pyrroloquinolinequinone | — | 300 ng |
| "Tween 80" | — | 100 mg |

As samples for analysis, "ERENTAL" or parenteral nutrient manufactured by Ajinomoto Co., Inc., sardine meat and mackerel meat were used. 10 samples of 1 g each were taken and immersed in 10 ml of deionized water, respectively. After homogenization, heat treatment was conducted at 100° C. for 30 minutes in a hot water bath. The treated liquids were centrifuged and each supernatant was appropriately diluted. The dilutions were made test sample solutions.

*Alteromonas thalassomethanolica* YK 4007 FERM P-1401 was inoculated on the slant described above. After incubation at 30° C. for a day, the system was stored at 5° C. Upon use, the bacteria grown on the slant was suspended in Medium A and Medium B described above which contained methanol. After once rinsing with the same medium, respectively, dilution was performed in the same medium solution in such a manner that absorbancy (OD) became 0.3 at 610 nm. Thus, bacteria solutions for inoculation were obtained. A standard cyanocobalamin solution and test sample solutions were charged by 1 ml each into L-shaped tubes charged with 9 ml each of the aforesaid Medium A and Medium B containing methanol. Further 0.2 ml of the aforesaid bacteria solution for inoculation was added thereto followed by shake culture at 35° C. for 15 hours. The absorbancy of the culture solution was measured as an OD value at 610 nm to prepare a standard curve, based on which the amount of cyanocobalamin corresponding to the OD value of the test sample was determined. The results are shown in Table 2.

TABLE 2

| Sample | Methanol-Containing Medium A | | | Methanol-Containing Medium B | | |
|---|---|---|---|---|---|---|
| | Mean Value of 10 Samples (ng/g) | Maximum Value (ng/g) | Minimum Value (ng/g) | Mean Value of 10 Samples (ng/g) | Maximum Value (ng/g) | Minimum Value (ng/g) |
| ERENTAL | 8.5 | 9.0 | 8.0 | 8.7 | 8.9 | 8.6 |
| Sardine meat | 55.3 | 59.8 | 50.1 | 53.8 | 54.3 | 52.9 |
| Mackerel meat | 10.2 | 10.9 | 9.3 | 9.8 | 10.1 | 9.7 |

EXAMPLE 2

The amount of cyanocobalamin contained in "ERENTAL" was quantitatively assayed in a manner similar to Example 1 except that a medium shown in Table 3 was used as a basal medium, a medium for quantitative assay supplemented with pyrroloquinoline-quinone having a concentration shown in Table 4 and "Tween 80" was used and "ERENTAL" or parenteral nutrient as used in Example 1 was used.

TABLE 3

| Medium for quantitative assay: | |
|---|---|
| $KH_2PO_4$ | 1.0 g |
| $K_2HPO_4$ | 3.0 g |
| $(NH_4)_2SO_4$ | 1.0 g |
| $MgSO_4.7H_2O$ | 0.3 g |
| NaCl | 30.0 g |
| $NaS_2O_3.5H_2O$ | 10.0 mg |
| $ZnSO_4.7H_2O$ | 30.0 μg |
| $FeSO_4.7H_2O$ | 5.0 mg |
| Methanol | 5.0 ml |
| Water | 1000 ml |
| pH 6.8 | |

The results are shown in Table 4.

TABLE 4

| Addition Concentration | | | | |
|---|---|---|---|---|
| Pyrroloquinoline-quinone (ng/100 ml) | Tween 80 (ng/100 ml) | Mean Value of 10 Samples (ng/100 ml) | Maximum Value (ng/100 ml) | Minimum Value (ng/100 ml) |
| 0 | 0 | 8.5 | 9.0 | 8.0 |
| 8 | 0 | 8.5 | 8.9 | 8.0 |
| 10 | 1 | 8.5 | 8.6 | 8.4 |
| 30 | 10 | 8.5 | 8.6 | 8.4 |
| 60 | 20 | 8.5 | 8.6 | 8.4 |
| 75 | 20 | 6.2 | 6.4 | 6.0 |

While the invention has been described in detail and with reference to specific embodiments thereof, it will be apparent to one skilled in the art that various changes and modifications can be made therein without departing from the spirit and scope thereof.

What is claimed is:

1. A method for the quantitative assay of vitamin $B_{12}$ in a substance containing vitamin $B_{12}$ comprising:

adding marine methanol-utilizing bacteria having vitamin $B_{12}$ auxotrophy to a medium for quantitative assay of said bacteria containing pyrroloquinoline-quinone and a polyoxyethylene sorbitan fatty acid ester;

adding a standard dilution of vitamin $B_{12}$ in a serial concentration to a first portion of said medium to culture said bacteria in said first portion;

measuring the absorbancy of said first portion as standard dilution OD values to determine the degree of growth of said bacteria as a function of vitamin $B_{12}$ concentration;

preparing a standard linear curve of absorbancy versus $B_{12}$ concentration based on said measurements;

adding a test substance to a second portion of said medium to culture said bacteria in said second portion;

measuring the absorbancy of said second portion as a test substance OD value to determine the degree of growth of said bacteria; and comparing the test substance OD value with said standard linear curve to quantitatively determine the $B_{12}$ concentration in said test substance.

2. A method as in claim 1, wherein said medium contains 10 to 60 mg of pyrroloquinoline-quinone per 100 ml of medium and 1 to 20 mg of polyoxyethylene sorbitan fatty acid ester per 100 ml of medium.

3. A method as in claim 1, wherein said bacteria is *Alteromonas thalassomethanolica* YK 4007.

4. A quantitative assay reagent kit for determining the quantity of vitamin $B_{12}$ in a substance containing vitamin $B_{12}$ comprising a first vial having sealed therein a dry viable bacteria composition of marine methanol-utilizing bacteria having $B_{12}$ auxotrophy for inoculation; a second vial having sealed therein a medium for quantitative assay of said bacteria containing pyrroloquinoline-quinone and a polyoxyethylene sorbitan fatty acid ester; and a third viral having sealed therein a standard dilution of vitamin $B_{12}$ having a serial concentration.

5. A kit as in claim 4, wherein said medium contains 10 to 60 mg of pyrroloquinoline-quinone per 100 ml of the medium and 1 to 20 mg of polyoxyethylene sorbitan fatty acid ester per 100 ml of medium.

6. A kit as in claim 4, wherein said bacteria is *Alteromonas thalassomethanolica* YK 4007.

* * * * *